United States Patent [19]

Herpers

[11] 4,390,020
[45] Jun. 28, 1983

[54] IMPLANTABLE MEDICAL DEVICE AND POWER SOURCE DEPLETION CONTROL THEREFOR

[75] Inventor: Lodewijk-Jozef Herpers, Kerkrade-West, Netherlands

[73] Assignee: Medtronic, Inc., Minneapolis, Minn.

[21] Appl. No.: 235,069

[22] Filed: Feb. 17, 1983

[51] Int. Cl.³ .............................................. D61N 1/36
[52] U.S. Cl. ........................ 128/419 PG; 128/419 PT
[58] Field of Search .................. 128/419 PG, 419 PS, 128/419 PT

[56] References Cited

U.S. PATENT DOCUMENTS

| | | | |
|---|---|---|---|
| 3,738,371 | 6/1973 | Raddi | 128/419 |
| 3,789,854 | 2/1974 | Lee | 128/419 |
| 3,901,247 | 8/1975 | Walmsley | 128/419 |
| 4,091,817 | 5/1978 | Thaler | 128/419 |
| 4,102,345 | 7/1978 | Cannon | 128/419 |
| 4,120,307 | 10/1978 | Jirak | 128/419 PT |
| 4,190,055 | 2/1980 | Walters et al. | 128/419 PT |
| 4,248,238 | 2/1981 | Joseph | 128/419 PG |

FOREIGN PATENT DOCUMENTS 2014858 9/1979 United Kingdom .

Primary Examiner—William E. Kamm
Attorney, Agent, or Firm—Joseph F. Breimayer; John L. Rooney; Robert C. Beck

[57] ABSTRACT

A programmable pulse generator capable of operating in several atrial and ventricular pacing modes having atrial and ventricular sense amplifiers and output circuits, programmable memory and clock controlled digital timing circuits and a depletable power source. End-of-life sensing circuits detect first and second end-of-life depletion levels. Magnet activated end-of-life test circuitry responds to the presense of none, one or both of the end-of-life depletion level signals to alter the operating modes and pacing rates to indicate the orginally programmed mode and the level of depletion to an observer. Preferably, the pulse generator is operated in the asynchronous DOO or VOO modes and at non-programmed test rates to provide the indication.

30 Claims, 7 Drawing Figures

IMPLANTABLE MEDICAL DEVICE AND POWER SOURCE DEPLETION CONTROL THEREFOR

BACKGROUND OF THE INVENTION

1. Field of the Invention

This invention relates to operating mode and parameter changes in artificial implantable medical device, e.g. cardiac pacemakers, in response to and to indicate depletion of the device's sensing power source.

2. Description of the Prior Art

The implantable cardiac pacemaker, shown in U.S. Pat. No. 3,057,356 and subsequent patents permits innocuous, painless, long-term cardiac stimulation at low power levels by utilizing a small completely implanted transistorized and battery operated pulse generator connected via a flexible lead bearing an electrode directly in contact with cardiac tissue. Most pulse generators consist of a stimulating circuit and a sensing circuit both of which draw current from the battery. In the presence of complete heart block, an asynchronous pulse generator with only a stimulating circuit may be used, however, in most instances, noncompetitive triggered or inhibited pulse generators having the sensing circuit are preferred and dominate the pacemaker market. The demand, synchronous or triggered pulse generators are especially useful in patients with spontaneous cardiac activity because of their ability to sense intrinsic cardiac rhythm (atrial or ventricular depending on variety and electrode position), and to alter the pacemaker output accordingly. Such pacemakers are shown for example, in U.S. Pat. Nos. 3,253,596 (P-wave synchronous), 3,478,746 (ventricular inhibited) and are described in the pacing literature.

More recently, attention has been paid to the physiological aspects of cardiac pacing therapy and particularly to pacing systems for maintaining synchronous atrial and ventricular depolarization of the heart. In early atrial synchronized (or A-V synchronous) pacing, atrial depolarization is sensed through one electrode, and after an appropriate delay the ventricle is paced through a different electrode, thereby restoring the normal sequence of atrial and ventricular contraction and allowing the pacer to respond to physiologic needs by increasing its rate. Below a predetermined minimal atrial rate, however, the pacemaker reverts to its basic ventricular pacing rate. In atrial synchronous, ventricular inhibited pacers of the type described in U.S. Pat. Nos. 4,059,116 and 3,648,707, the ventricular depolarizations are also sensed and inhibit or reset the timing of the ventricular stimulating pulse generator.

A more complex method of restoring synchrony is by the atrial ventricular sequential pacing of the type described in U.S. Pat. No. 3,595,242 and subsequent patents which possess atrial and ventricular pulse generators and associated electrodes and a ventricular sensing circuit. In atrial ventricular sequential pacing, the atria and ventricles are paced in proper sequence, the atrial and ventricular pulse generator timing circuits being reset on sensing spontaneous ventricular activity.

Finally, U.S. Pat. No. 4,312,355, by Hermann D. Funke, (assigned to a subsidiary company of the assignee of the present invention), discloses a pacemaker which, if required, may stimulate the atrium and/or ventricle on demand and which is able to maintain synchrony as the sensed atrial rate increases. A pacemaker of this type is capable of distinguishing between bradycardia and normal heart function and to provide atrial and/or ventricular pacing in the following modes: inhibited in the case where the atrium and ventricle beat at a sufficient rate; atrial demand in instances where the atrium is beating at an insufficient rate and must be stimulated whereas the ventricle properly follows; atrial synchronous when the atrium depolarizes at a sufficient rate but the ventricle does not follow within a prescribed A-V interval; and demand in both chambers when neither the atrium and the ventricle spontaneously depolarize at the desired rate.

All of the demand pacemakers of the types described above comprise ventricular and/or atrial timing circuits which may be a simple oscillator of the early designs or the complex, programmable, digital timing circuit of the type disclosed, for example, in the commonly assigned U.S. Pat. No. 4,230,120, an analog sense amplifier circuit of the type disclosed, for example, in the U.S. Pat. No. 4,266,551, by Marc T. Stein, and an analog output circuit of the type disclosed, for example, in the copending U.S. Ser. No. 184,777 filed Sept. 8, 1980 in the name of David L. Thompson, all assigned to the assignee of the present invention. The inputs of the respective sense amplifiers and the output capacitances of the output circuits are commonly coupled to the respective atrial or ventricular sense amplifiers and through pacing leads to the electrodes coupled to the patient's heart.

Such medical devices as the demand pacemakers of the types described above are powered by depletable power sources or batteries which deplete from a beginning of life (BOL) to an end of life (EOL) voltage and current condition. The depletion reduces the current and voltage available to power the various components of the pulse generator and provide an adequate stimulation energy leading to either loss of capability of the device or capture of the patient's heart. To alert the patient or physician of the condition of the battery, prior art pulse generators have provide end-of-life indicator circuits, usually activated by a magnetically actuated reed switch, which cause the pulse generator to operate in an asynchronous mode at a rate which differs from the rate provided at BOL in proportion to the power source depletion or to a predetermined EOL rate upon depletion or to a predetermined EOL rate upon depletion to a selected EOL energy level. Such prior art pulse generators of the type described in the aforementioned U.S. Pat. No. 4,230,120 possess such EOL circuitry for indicating to the physician the state of depletion of the power source. In a multi-programmable multi-mode medical device of the type described herein, several modes and operating parameters of the device may be selectively programmed. In the atrial and ventricular pacemaker of the type described herein, the energy drain on the power source is accentuated by the complexity and number of components in the circuitry and by the A-V sequential pacing output pulses which over the same period of time, at full pacing, draw current more rapidly from the battery than a conventional single chamber demand pacemaker. These characteristics of the pulse generator in which the present invention is embodied require a more complex and graduated manner in which the power source depletion may be monitored under several operating conditions.

SUMMARY OF THE INVENTION

Accordingly, in recognition of the above-stated characteristics of the more complex medical devices, the present invention provides a battery depletion indicator which can be selectively interrogated to cause the medical device to operate in pre-selected modes and rates which indicate the mode in which the device is programmed and the depletion level of the power source.

Within the context of an implantable pacemaker pulse generator incorporating cooperating analog and digital circuitry for the generation and application of stimulating pulses to the atrium and/or the ventricle of the patient's heart, the present invention is directed to the EOL indicating circuitry and method of operation of the pulse generator in response to its interrogation which causes the pulse generator to operate in pre-selected modes and at pre-selected pacing rates within a range of BOL power source energy and upon depletion to EOL energy levels. Briefly, the power source depletion indicating circuitry and method of the present invention contemplates the operation of the pulse generator in an asynchronous pacing mode upon closure of a reed switch in response to an applied magnetic field and the selection of a predetermined pacing rate from a number of possible pacing rates to indicate to the observing physician that the power source is within the BOL range or has depleted in energy to one or more EOL depletion levels. In certain programmed modes of operation of the pulse generator wherein both the atrium and ventricle can be stimulated by atrial and ventricular output pulses, the closure of the reed switch effects an asynchronous A-V pacing mode. When the pulse generator is alternately programmed in the modes wherein atrial pacing cannot take place, the pulse generator is operated in the asynchronous ventricular pacing mode during testing of the depletion level. In a preferred embodiment of the invention, first and second EOL levels indicating imminent battery depletion and final battery depletion, respectively, cause the pulse generator (upon application of the magnetic field) to change its operating mode. At the second EOL level, the operating mode is changed by application of the magnet from its programmed mode to the ventricular demand (VVI) mode to conserve remaining battery energy. The pacing rate is also changed to the second EOL test rate.

As a further feature of the invention, at the BOL and EOL condition, the programmed modes may be distinguished from one another by the selection of the pacing rate and mode. The modes are changed to the A-V asynchronous (DOO) mode or the ventricular asynchronous (VOO) mode depending on the programmed modes. The programmed rate may also be changed to a third preset rate different from any possible programmable rate. In this manner, the combination of the observed rate and the observed mode indicates to the physician the battery condition and programmed mode of operation of the pulse generator.

The foregoing and additional advantages and characterizing features of the present invention will become clearly apparent upon reading of the ensuing detailed description of an illustrative embodiment thereof together with the included drawings depicting this theme.

DESCRIPTION OF THE PREFERRED EMBODIMENT

Figures 1, 1A, 1B:
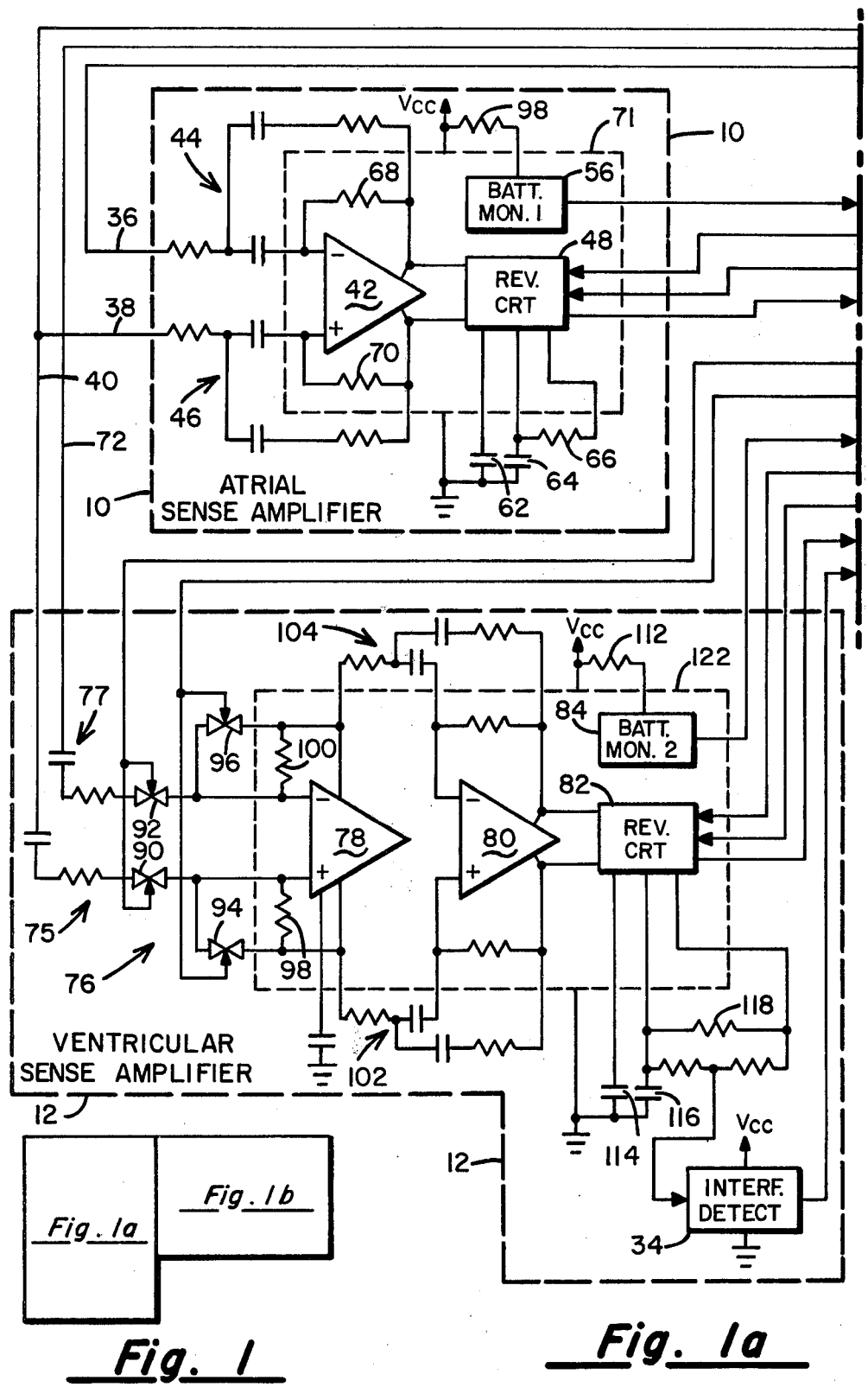
FIG. 1 shows the arrangement of FIGS. 1a and 1b which in turn show a block circuit diagram of the dual chamber pacemaker of the present invention.
Figure 1B:
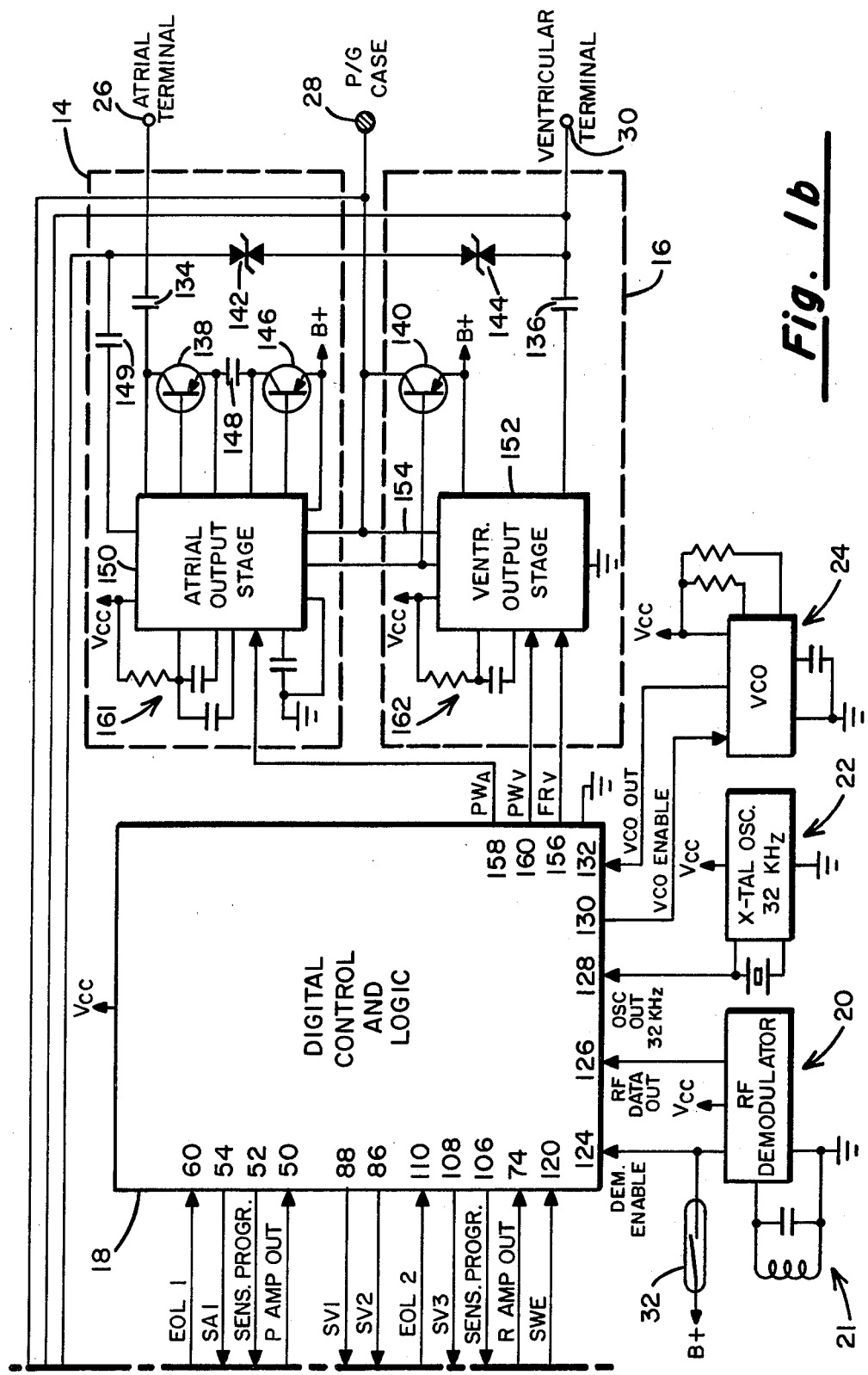

The depletion mode operation of the pulse generator of the present invention will be explained in detail after the following descriptions of the dual chamber DDD pacemaker in which it is embodied.

The dual chamber pacemaker of the present invention possesses five basic components in addition to the necessary power supply and leads for conducting electrical signals between the patient's heart and the pacemaker pulse generator. These components are an atrial sense amplifier, a ventricular sense amplifier, an atrial output stage, a ventricular output stage, and a digital controller circuit possessing programmable memory and logic circuits which time the production of atrial and/or ventricular stimulating output pulses as a function of the P waves sensed by the atrial sense amplifier, R waves sensed by the ventricular sense amplifier, parameter and mode data stored within the memory, the status of the power source voltage, and the condition of a reed switch which may be effected by an external magnetic field. It is contemplated that in the preferred embodiment of this invention, the pulse generator would be contained within a sealed metallic container electrically connected to the output stages to act as an indifferent electrode and a pair of output connectors or terminals adapted to be coupled by way of leads from the output terminals extending to the atrium and ventricle of the patient's heart.

It is contemplated that the dual chamber pacemaker of the present invention may automatically operate in several different pacing modes depending on the presence or absence of sensed atrial and/or ventricular depolarizations, that is P waves and/or R waves, in a manner described generally for example in the above-mentioned U.S. patent application Ser. No. 120,237, In this context, it is contemplated that several modes of operation may automatically take place depending on the condition of the patient's heart.

Generally, if neither P-waves nor R-waves are present in the atrial and ventricular escape intervals set by the timing circuitry of the pacemaker, it will function in the dual chamber, A-V sequential fixed rate mode (DOO mode as this mode and others referred to herein are designated in the Report of the Inter-Society Commission for Heart Disease Resources in *Circulation*, Vol. L., October, 1974.) If P-waves are not present, but R-waves recur from time to time within the A-V delay interval, the device operates in the A-V sequential demand or DVI mode. If P-waves are present, this device operates in the atrial synchronous or VAT mode in the absence of R-waves sensed within the A-V escape interval or in the atrial synchronous ventricular inhibited (ASVIP) or VDT/I mode when R-waves recur within the A-V interval.

In addition it is contemplated that the dual chamber pacemaker of the present invention may be externally programmed to operate in a number of different modes including: the fully automatic dual chamber, or DDD mode described above, in which the atrial and ventricular sense amplifiers and the atrial and ventricular output stages are fully operational; in the atrial-ventricular sequential pacing mode, or DVI mode, wherein atrial and ventricular stimulating pulses are provided in timed relationship to one another in the absence of sensed ventricular depolarization; in the atrial synchronous, ventricular inhibited (ASVIP) mode, or the VDT/I mode, wherein the sensed atrial deplarizations cause the pulse generator to deliver a ventricular stimulation pulse unless a spontaneous or conducted ventricular depolarization is detected by the ventricular sense amplifier prior to the timing out of a suitable A-V delay period; or the ventricular demand pacing mode, the VVI mode, wherein the atrial sense amplifier and atrial output stages are not employed.

In addition it is contemplated that the pulse generator can be programmed to operate in the atrial asynchronous mode (AOO), the ventricular asynchronous mode (VOO), or the atrial ventricular asynchronous mode (DOO), by selectively programming pulse width to zero and sensitivity to infinite to arrive at these resulting combinations.

Turning now to FIGS. 1a and 1b, there is shown an atrial sense amplifier 10, ventricular sense amplifier 12, atrial output stage 14, ventricular output stage 16, digital control and logic circuit 18, and three further circuits, the RF demodulator circuit 20 for receiving remotely applied programming signals and magnetic field test signals, a crystal oscillator 22 for providing the basic clock frequency for the digital control and logic circuit 18, and a voltage controlled oscillator (VCO) circuit 24 for timing certain operations of the digital control and logic circuit 18. The atrial sense amplifier 10 is coupled between the atrial lead terminal 26 and the case terminal 28 for sensing atrial depolarizations, or P waves. The ventricular sense amplifier 12 is similarly coupled to the case terminal 28 and the ventricular pacing lead terminal 30, for sensing ventricular depolarizations, or R waves. The digital control and logic circuit 18 is coupled to the output terminals of the atrial and ventricular sense amplifiers to receive the atrial amplifier output signal at terminal 50 and the ventricular amplifier output signal at terminal 74, to process the signals in accordance with the mode to which the pacemaker is programmed and the parameters of atrial and ventricular timing escape intervals and to produce, if appropriate, atrial pace initiate signals PWA and ventricular pace initiate signals PWV which are respectively coupled to input terminals of the atrial output stage 14 and the ventricular output stage 16 to initiate respective atrial and ventricular stimulating pulses. The production of the atrial and/or ventricular initiate pulses is dependent upon the presence or absence of sensed atrial and/or ventricular depolarizations of the heart within certain escape intervals established by parameter data stored in memory within the digital control and logic circuit 18 and dependent upon whether or not the reed switch 32 is open or closed by the application of an external magnet or on the condition of interference detector 34 within the ventricular sense amplifier 12 which responds to noise signals picked up by the ventricular sense amplifier. Ignoring for the moment the possibility of the closure of the reed switch 32 or interference, and turning to the operation of the circuit in the DDD mode, the pulse generator will pace at a programmable lower rate if neither P waves nor R waves are sensed within the escape intervals established by lower rate data stored in memory. The A-V interval between the production of atrial and ventricular initiate signals by the digital control and logic circuit 18 is similarly programmable and, under these conditions, the total operation of the pacemaker is characterized as A-V sequential, demand pacing.

If a P wave is sensed by the atrial sense amplifier 10 within the programmed atrial escape interval, (corresponding to a programmable lower rate), the digital control and logic circuit 18 will not produce an atrial pace initiate signal, but instead will commence the timing of the A-V interval. If an R wave is sensed by the ventricular sense amplifier 12 prior to the expiration of the A-V interval, the ventricular pacing initiate signal is similarly not produced, and all timing intervals will be reset. But if an R wave is not sensed prior to the completion of the A-V interval, a ventricular pace initiate pulse will be provided by the digital control and logic circuit to initiate the production of a ventricular pacing stimulus at the end of the delay.

If the memory within the digital control and logic circuit 18 is programmed to the VVI mode, the atrial sense amplifier output signal is ignored, and the atrial output initiate signal is not produced. Thus, the digital control and logic circuit 18 responds only to R waves sensed by the ventricular amplifier 12 and produces only ventricular pace initiate signals in the absence of an R wave occurring prior to the expiration of the ventricular escape interval.

If the device is programmed in the DVI mode, the atrial output signal of the atrial sense amplifier 10 is similarly ignored. However, the atrial output stage and the ventricular output stage receive atrial and ventricular pace initiate signals at the programmable lower rate and separated by the A-V interval. If an R wave is sensed during the escape interval and following the refractory period of the ventricular sense amplifier, the lower rate timing is reset. If an R wave is sensed prior to the completion of the A-V interval and following the delivery of an atrial stimulating pulse to the heart, then the ventricular pace initiate signal is inhibited or not delivered, and the lower rate escape interval is again reset.

In the atrial synchronous ventricular inhibited, or VDT/I mode, P waves recurring at a rate exceeding the programmable lower rate, are sensed by the atrial sense amplifier and processed by the digital control and logic circuit 18 to commence the A-V timing interval. Again, if an R wave is sensed prior to the completion of the A-V interval, the ventricular pacing output is inhibited and all timing circuits will be reset. But, if an R wave is not sensed prior to the completion of the A-V interval, a ventricular pacing stimulus will be provided in response to a ventricular pace initiate signal at the end of the A-V interval. A sensed R wave occurring within the programmed lower rate escape interval and after the refractory period since the last ventricular depolarization or stimulating pulse, will be processed by the digital control and logic circuit 18 to restart the lower rate timing interval.

The above modes of operation may be selected by the physician to conform the operation of the pacemaker to the patient's condition or the condition of the atrial or ventricular pacing leads. Ordinarily it would be expected that the pacemaker would be left operating in the fully automatic dual chamber or DDD mode, with the lower rate interval, A-V timing interval and other parameters of operation of the device being selected and programmed to conform to the patient's condition.

Turning now to the specific elements shown in FIG. 1, the atrial sense amplifier 10 is coupled to the atrial lead 26 and the pulse generator 28 through conductors 36 and 38, 40 respectively. The conductors 36 and 38 are coupled to the negative and positive input terminals of differential amplifier 42 to a balanced resistance and capacitive network circuit 44 and 46 connected between the input and output terminals of the differential amplifier 42. The differential output signal of the amplifier 42 is coupled to a reversion circuit 48 which is designed to detect natural heart depolarizations in the presence of continuous noise signals. The reversion circuit 48 responds to the amplified signal to produce a P wave output signal which is applied to the input terminal 50 of the digital control and logic circuit 18.

Atrial sense amplifier 10 depicted in FIG. 1 also shows a pair of reversion capacitors 62, 64 and a trim resistor 66 coupled to the reversion circuit 48. The differential amplifier 42, the reversion circuit 48, the battery monitor 56 and gain control resistors 68 and 70 can be packaged within a linear circuit chip 71 coupled to source voltage Vcc and system ground. The atrial sense amplifier as described conforms substantially to that depicted and described in the aforementioned U.S. patent application Ser. No. 957,825.

Turning to the ventricular sense amplifier 12, it is coupled by conductors 40 and 72 to the pulse generator case 28 and the ventricular lead 30, respectively, and at its output terminal 74 to the digital control and logic circuit 18. The ventricular sense amplifier contains a FET switch array 76, a first differential amplifier 78, a second differential amplifier 80, a reversion circuit 82, a second battery monitor circuit 84, and various biasing and filtering components. In general terms, the ventricular sense amplifier 12 is designed to detect ventricular depolarizations and to avoid detecting atrial stimulating pulses delivered by the atrial output stage 14. To that end, the ventricular sense amplifier 12 is provided with a FET switch array 76 and the first differential amplifier 78 coupled between the output terminals 28 and 30 and the input terminals of a second differential amplifier 80.

In general terms, the FET switch array 76 possesses a first pair of series switches of transmission gates controlled by a first switch signal SV1 at terminal 88 and a second switch signal SV2 at terminal 86. The transmission gates 90 and 92 are coupled in series with the positive and negative input terminals of differential amplifier 78 and the transmission gates 94 and 96 are coupled in parallel with gain control resistors 98 and 100 coupled between the input and output terminals of amplifier 78. Ordinarily, in the absence of signals SV1 and SV2, the gates 90 and 92 are closed and the gates 94 and 96 are open. Thus, the differential amplifier 78 is ordinarily coupled to series connected RC filter circuits 79, 77 and the conductor 72 and 40 to the ventricular lead 30 and pulse generator case 28 respectively, and the gain of the differential amplifier 78 is controlled by the value of the resistors 98 and 100. Thus, signals appearing on the conductors 40 and 72 are differentially amplified in the balance differential amplifier 78 and coupled to RC circuits 102 and 104 to the second differential amplifier 80. As in the atrial sense amplifier 10, the output signals are coupled to a reversion circuit 82 to provide an R wave amplifier output signal at the terminal 74 of the digital control and logic circuit 18.

The signals SV1 and SV2 are generated just prior (e.g. 2 clock pulses earlier) to the generation of an atrial pace initiate pulse PWA which is delivered to the atrial output stage 14. The signals SV1 and SV2 are applied to the transmission gates 90-96 to open the gates 90 and 92 and close the gates 94 and 96 to disconnect the input terminal of the differential amplifier 78 from the conductors 40 and 72 and lower the amplifier's gain by shorting out the resistors 98 and 100. After a certain interval, such as 8 ms, the signal SV1 ceases, thus restoring the connection of the differential amplifier 78 to the conductors 40 and 72. A short time thereafter, such as 3.9 ms later, the signal SV2 ceases and the full gain of the differential amplifier 78 is restored. This operation insures that the atrial output pulse reflected on the pulse generator case terminal and terminal 30 does not itself cause the ventricular sense amplifier to mistakenly produce an output pulse.

The reversion circuit 82 also includes circuitry which upon receiving an appropriate programming signal from the digital control and logic circuit 18 can adjust the sensitivity of the ventricular sense amplifier 12 through a signal on terminal 106, and circuitry for responding to a further switch signal SV3 at terminal 108 for blanking the ventricular sense amplifier 12 following the sensing of an earlier ventricular depolarization or the production of a ventricular pace initiate signal. The ventricular sense amplifier 12 further comprises a second battery monitoring circuit 84 for producing a second end-of-life signal EOL2 at terminal 110 when source voltage Vcc falls below a further lower reference voltage Vref2 established by the monitoring circuit 84. In addition, the ventricular sense amplifier 12 possesses the first and second reversion circuit capacitors 114 and 116, sensitivity trimming resistors 118 and an interference detecting circuit 34 for producing a signal SWE at terminal 120 when interference causes the capacitor 116 of reversion circuit 82 to become charged to a certain level. The control signal SWE at terminal 120 indicates to the digital control and logic circuit 18 that interference is present and causes it to provide certain control signals to insure that the reversion circuit 82 does not itself falsely produce an R wave output pulse at terminal 74 on the resumption of applied interference signals following the connection of the differential amplifier 78 to terminals 28 and 30 in the manner described above.

The components of the ventricular sense amplifier 12 with the exception of the switch array 76 and the first differential amplifier 78 and interference detector 34 are shown and described in the commonly assigned, co-pending U.S. patent application Ser. No. 252,537, filed Apr. 9, 1981 by Marc T. Stein. It is contemplated that the first and second differential amplifier 78 and 80, the reversion circuit 82, the battery monitor circuit 84 and certain of the resistances would be constructed in a linear IC circuit 122. Filter and bias circuit components 75, 77, 102, 104, 112, 118 are selected to provide the appropriate frequency response and specification as is well known in the art.

The reed switch 32 is shown coupled between the input terminal 124 and battery voltage B+. The closure of the reed switch 32 applies battery voltage to the terminal 124 and additional control and logic circuit 18 responds thereto to perform certain functions to be described in greater detail later, and to the RF demodulator 20 for enabling the RF demodulator 20 to demodulate applied RF signals detected in the tank circuit 21 and produce RF data output signals at the terminal 126.

Also shown in FIG. 16 is a crystal oscillator 22 for providing the principal or fast clock signal for counting operations of digital control and logic circuit 18.

A VCO circuit 24 comprising a voltage controlled oscillator and its associated trimming components which provides the clock frequency for the output pulse widths is also shown in FIG. 16. The VCO circuit 24, upon receiving a VCO ENABLE signal at terminal 130, applies the VCO output signal to the terminal 132 of the digital control and logic circuit 18, the frequency of the VCO output signal being dependent on the then prevailing source voltage Vcc and the digital control and logic circuit 18 produces the VCO ENABLE signal at the terminal 130. The VCO circuit 24 responds and provides the VCO OUT signal at the terminal 132. The digital control and logic circuit 18 responds to the VCO OUT signal to employ the VCO signal as a timing signal in timing the widths of the atrial and ventricular pace initiate signals, thereby effecting an increase in the width of the atrial and ventricular stimulating pulses from the width programmed in memory within the digital control and logic circuit 18. A general operation of the VCO circuit 24 and the digital control and logic circuit 18 for effecting this mode of operation of the device is described in the aforementioned U.S. Pat. No. 4,230,120.

The atrial and ventricular output stages 14 and 16 each comprise defibrillation protection diodes 142 and 144 and an output capacitor 134 and 136 respectively connected to the atrial lead terminal 26 and ventricular lead terminal 30. In both instances, the output capacitors are charged to battery voltage B+ and are discharged through transistor switches (not shown) within the atrial output stage 150 and the ventricular output stage 152, respectively, and commonly through the conductor 154 and case terminal 28 through the hear tissue and back to the terminals 26 and 30, respectively. The ventricular output capacitor 136 is recharged through conduction of transistor 140 while the stored output capacitor 134 is recharged through the transistors 138, 146, and capacitor 148 and in relation to the voltage on reference capacitor 149. The recharge cycle is under the control of a fast recharge control signal FRV developed by the digital control and logic circuit 18 at terminal 156. A description of the atrial output circuit and the fast recharge operation is disclosed in commonly assigned and co-pending U.S. patent application Ser. No. 252,538, filed Apr. 9, 1981, in the name of Marc T. Stein.

The pulse widths of the atrial and ventricular stimulating pulses are established by the widths of the atrial and ventricular output initiate signals PWA and PWV at terminals 158 and 160 respectively. The atrial and ventricular output stages 150 and 152 are coupled between regulated supply voltage Vcc and system ground through respective biasing components 161 and 162 in a manner well known in the art.

Figures 2, 2A:
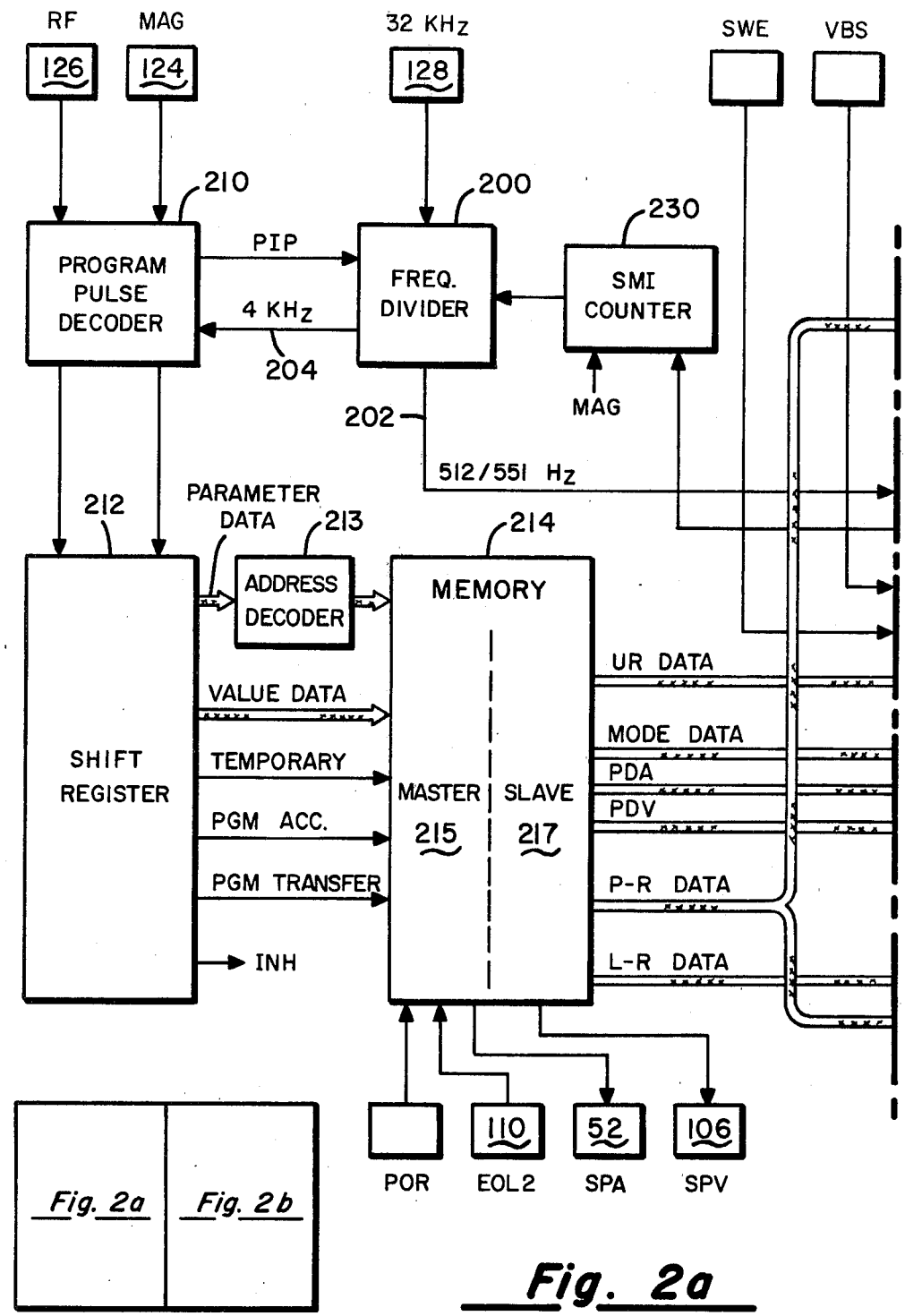
FIG. 2 shows the arrangement of FIGS. 2a and 2b which in turn show a block circuit diagram of the digital controller circuit employed in the FIG. 1 circuit.
Figure 2B:
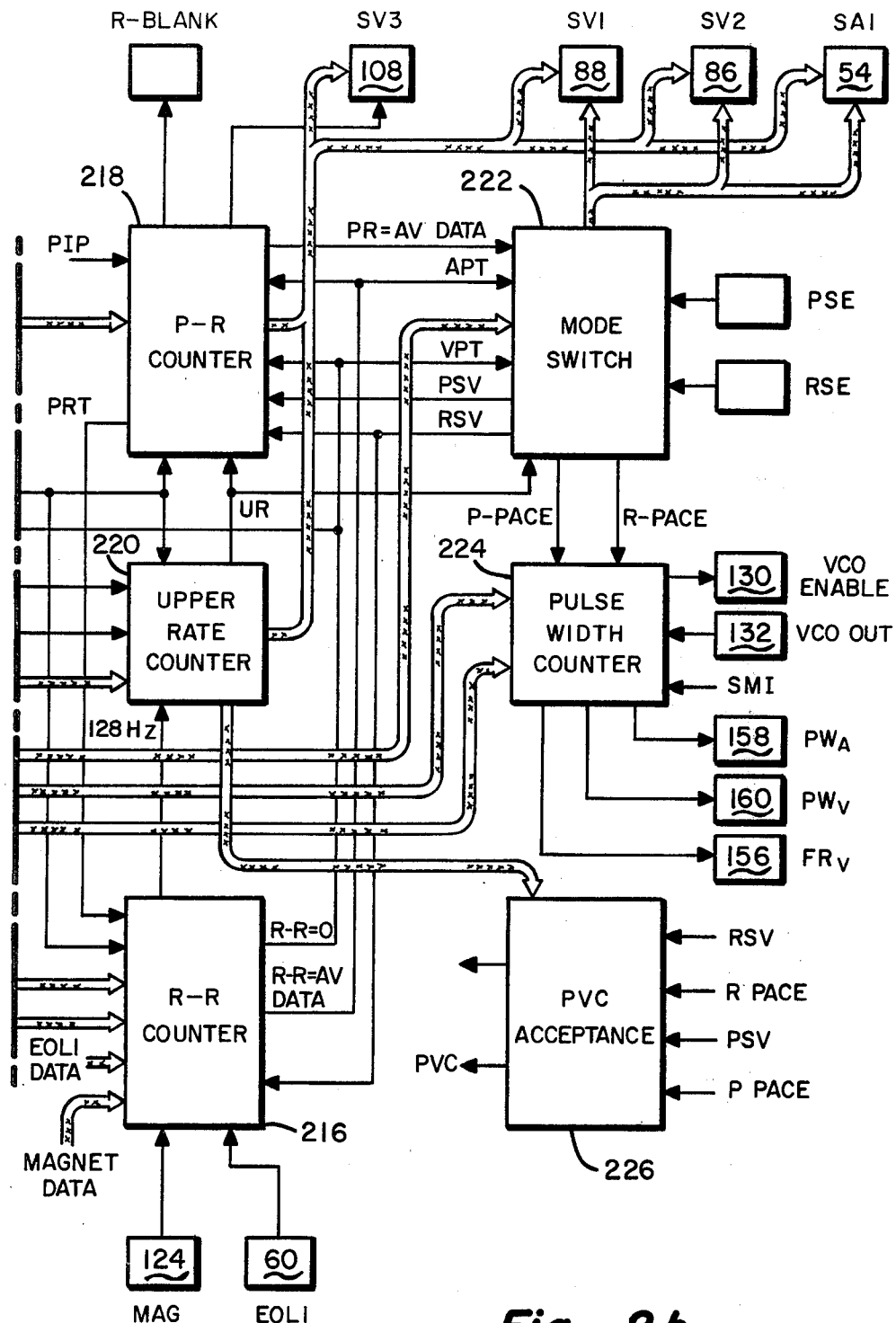

The digital control and logic circuit 18 is depicted in greater detail in FIG. 2. In general terms, FIG. 2 shows the circuit components for receiving externally applied programming signals for programming the modes and parameters of operation of the digitally controlled pacemaker of FIGS. 1a and 1b, memory storage for storing the programming signals, various counting circuits for timing the lower rate escape interval, the upper rate maximum allowed pacing rate, the A-V time delay, and other intervals for setting the pulse width duration of the atrial and ventricular output initiate signals and atrial and ventricular sense amplifier sensitivities, and switching circuitry for controlling the modes of operation of the pacemaker. The circuit of FIGS. 2a and 2b is implemented in digital logic components and circuits of said type shown in the aforementioned U.S. Pat. No. 4,230,120. Distinctions arise from the fact that the circuit disclosed in that application is intended for control of a ventricular demand or VVI mode pacemaker, and the present invention is implemented in the context of a programmable, fully automatic dual chamber pacemaker normally operable in the DDD mode.

Referring to FIGS. 2a and 2b in greater detail, the 32 kHz crystal oscillator frequency is applied at terminal 128 to a frequency divider circuit 200 which produces a 512 Hz slow clock signal at terminal 202 and a 4 kHz decoding signal at terminal 204. The 4 kHz signal is applied to the program pulse decoder 210 which decodes incoming RF signals appearing at terminal 126 to separate logic 1 and logic 0 signals from one another. The program pulse decoder 210 applies the decoded data signals to the D input terminal of the shift register 212 and a clocking signal to the C input terminal of the shift register 212. The shift register 212 accumulates the decoded data signals and performs parity checking to assure that the serially received incoming data signals comprise properly formed programming words.

The clock frequency circuit and the content and format of the received data words are similar to that described in the aforementioned U.S. Pat. No. 4,230,120. In general terms, the decoded data signal at terminal D of shift register 212 is a series of 33 pulse signals separated by short and long intervals defining 32 logic 1 or logic 0 data bits. The 32 bit data words consists of four parts, each of which is 8 bits in length. The four parts are the parameter code, date or value code, access code and parity code and are generated in that order, the least significant bit first. The parameter portion of the data signal defines one of several parameters (including modes of operation) to be modified and whether the modification is to be in a temporary or permanent matter, if that choice is available. The several parameters include "mode" comprising threshold check mode, the fully inhibited mode, the DDD mode, the DVI mode, the VDT/I mode, the VVI mode, the sensitivities of the sense amplifiers, the A-V period, the lower pacing rate, and the upper pacing rate, the atrial and ventricular stimulation pulse widths. Of these parameters, the inhibit and threshold check parameters can only be done in a temporary mode whereas all the others can either be permanently or temporarily programmed. The programming parameter code and value codes are similar to but not necessarily the same as those set forth in the aforementioned U.S. Pat. No. 4,230,120, and in any event can be arbitrarily selected by those skilled in the art. The access code will, of course, differ from codes employed to program the pulse generator types. It will be noted that in the context of a dual chamber pacemaker, it will of course be necessary to increase the total number of serial transmissions of the 32 bit word data to effect programming of, for example, the sensitivity of the atrial and ventricular sense amplifiers.

The shift register 212 contains eight access code storing stages, access decoding and parity bit checking logic circuitry for insuring that the access code is correct and that the program word possesses proper parity, five parameter code shift register states for storing the five most significant bits of the eight bit parameter code (the first three bits of the eight bit parameter code are not used whatsoever and are always generated at logic 0 bits), and eight data or value code storage shift register stages for storing eight bits which define a particular value for the parameter selected. Ten further storage register stages and logic circuitry coupled parameters and data storage stages and certain stages of memory 214 effect the transfer of the parameters, e.g., the mode, lower rate, A-V interval, upper rate, atrial pulse width, ventricular pulse width, temporary atrial and ventricular pulse width and atrial and ventricular sense amplifier sensitivities.

A "master" portion of each word is accepted in memory 214 when the access code and parity check are found valid and all 32 bits of the program word is received. Further program transfer logic circuitry within the shift register 212 affects the shifting of the parameter data from the shift register 212 to the "master" register of the memory 214 in the permanent or temporary programming modes described hereinbefore. On acceptance of the transferred word, the shift register stages of shift register 212 are verified to accept the subsequently applied programming signal. Through serial application of the programming signals, all parameters and parameter values are stored within the memory 214, except that (1) if the parameter is "mode" and the value is "inhibit", then the word is not transferred but is applied to the circuit to inhibit all operations; and (2) if the parameter is "sensitivity" and the value code contains the indicator "new value", then only the word can be transferred.

The memory 214 contains address decode logic circuitry, master memory register 215 and slave memory register 217. Each decoded programming word from shift register 212 is transferred into the master register 215. Transfer of all contents of the master register 215 into the slave register 217 occurs only when the last word, indicated by a particular parameter code, has been stored in master portion 215, all the stored words possessed the valid access code and satisfied the parity check, and a ventricular pacing output pulse occurs after the last word and before receipt of any further words.

The master and slave registers also perform the function of temporary and permanent memory in the manner described in the aforementioned U.S. Pat. No. 4,230,120 for storing the various parameters and parameter values previously described and effecting the operation of the digital control and logic circuit 18 accordingly. Separate memory stages are devoted to the sensitivity of atrial and ventricular sense amplifiers, the programmable upper rates, the programmable lower rate or basic escape interval, the atrial and ventricular stimulation pulse widths, the A-V delay intervals, and data signifying the mode of operation of the device from among the various modes previously mentioned. The memory 214 furthermore possesses a hard wired lower rate for VVI mode that constitutes a basic safety rate should the power source energy momentarily dip below the circuits minimum operating requirements and also for use as one of the end-of-life test rates. Thus, the pulse generator will operate in a VVI mode at a predetermined rate, for example, 65 beat per minute, and at a predetermined pulse width if either condition exists. The EOL2 signal is applied at terminal 110 to the memory 214 and, under certain circumstances of operation to be described, its presence causes the hard wired safety rate to be substituted for the programmed rate upon magnet mode testing of the battery depletion.

The lower rate data is transferred by bus line from the memory 214 to the R-R or lower rate counter 216. The A-V interval data is transferred by bus to the P-R counter 218 and to the R-R counter 216. The upper rate data is transferred from the memory 214 to the upper rate circuit 220. The pulse width data, PDA and PDV for the control of the atrial and ventricular pulse widths is applied by bus lines from the memory 214 to the pulse width control circuit 224. The upper rate counter 220 is coupled by a bus line to the PVC acceptance circuit 226. The R-R interval counter 216 comprises a ten stage shift register counter at least eight stages of which are coupled through decoding logic circuitry to the memory stages of the memory 214 which specify the programmed lower rate values and the A-V values. The R-R counter stages constitute therefore a presettable down counter, which is downcounted under the control of the 512 Hz slow clock frequency or under the control of a magnet actuated clock frequency of approximately 551 Hz when the safety margin indicator (SMI) counter 230 is activated by the reed switch closure. The SMI counter 230 alters the number of stages of divider 200 to change the slow clock frequency to 551 Hz until it counts three VPT outputs of the R-R counter. The clock frequencies downcount the loaded counter until a first count is reached which, when decoded, provides an atrial pulse trigger signal APT and until a subsequent second count is recorded which, when decoded, provides a ventricular pulse trigger signal VPT. These signals APT and VPT are applied to the P-R counter 218 and the mode switch 222.

Thus during operation of the SMI counter 200, the pacing rate is increased by 10 percent to indicate closure of the reed switch. The SMI operation is therefore similar to that described in greater detail in the aforementioned U.S. Pat. No. 4,230,120.

The P-R counter 218 is an up counter that counts the 512 Hz slow clock signal from zero to the by A-V data count in memory 214. Upcounting commences when the signal PSV is received from mode switch 222 or the signal APT is received by the PR counter 218 and ceases when the count reaches a preselected number or the counters are reset by a sensed R wave.

The mode switch 222 also receives the signal APT and VPT and the mode data signals on a bus line from memory 214. The mode signal data sets the logic and switching circuits in the mode switch 222 to the modes previously described. Assuming that the memory 214 is programmed into the DDD mode, for example, the mode switch 222 responds to the signals APT and VPT to produce the P pace and R pace signals that are applied to the pulse duration counter 224. The pulse duration counter 224 responds to the P pace signal and the atrial pulse duration data signal PDA to produce the atrial output initiate signal PWA at terminal 158 and similarly responds to the R pace signal at the ventricular pulse duration data signal DDD to produce the ventricular output initiate signal PWV at the terminal 160. The output initiate signals PWA and PWV possess the pulse width signified by the programmed pulse duration signals PDA and PDV. In other programmable modes either P pace or the R pace signals are produced according to the mode indicated by the memory mode data. The mode switch 222 also provides signals PSE and RSE that enable or disable the atrial and ventricular sense amplifiers 10 and 12.

Under certain circumstances, the output initiate signals PWA and PWV may possess durations that deviate from the programmed pulse duration signals. This can occur when the battery or power source depletes in energy. The VCO 24 (FIG. 1) automatically changes its frequency with the source voltage, that is, it decreases as the voltage decreases. The VCO output signal at terminal 132 (FIG. 1b) is coupled to the PD counter 224 (FIG. 2b) and provides its clock signal. Thus, as the frequency slows, the time interval necessary to achieve the PDA or PDV count increases, thereby widening the output initiate pulses PWA and PWV. This operation is again like that described in the aforementioned U.S. Pat. No. 4,230,120.

The PVC acceptance circuit 226 responds to premature ventricular contractions sensed within the ventricular escape interval of the R-R counter to provide an output signal to reset the R-R counter timing. The circuit 226 also responds to the atrial and ventricular pacing events (P pace and R pace) developed by the mode switch 222 and the atrial and ventricular sense signals PSV and RSV to provide the ventricular sense amplifier 12 refractory period. The refractory period is decoded by the circuit 226 from the count on the upper rate counter 220, and is ordinarily 233 ms after a paced or sensed ventricular event. But, if a PVC is sensed and triggers circuit 226, then the upper rate counter count is decoded to provide a 342 ms refractory period.

In addition, if a P wave is sensed (PSV signal) following two successive sensed R waves (two RSV signals) or ventricular output pulses (R pace signals) or following an R pace and RSV signal, then the circuit 226 further establishes a 342 ms A-V delay interval commenced on the subsequently sensed atrial depolarization. This prolongation is employed to prevent a ventricular output pulse triggered by a sensed P-wave from possibly falling within the heart's vulnerable zone following the preceding premature ventricular contraction. This operation is further described in my commonly assigned copending U.S. patent application Ser. No. 235,232, filed Feb. 17, 1981.

Whenever the R-refractory is retriggered for 342 ms, the A-V counter is also disabled for 342 ms (bigeminy A-V disable). In case the device is programmed to VVI or DVI mode, ventricular amplifier outputs after ventricular blanking and before refractory ends cause another 125 ms ventricular blanking timer and the ventricular refractory period to be set again to 233 ms. Thus the digital reversion window will be equal to 108 ms This pacemaker as described hereinbefore has sense amplifiers 10, 12 and pulse output circuits 14, 16 for connection to both the ventricle and atrium. Two unipolar electrodes are coupled to terminals 26 and 30 and the can 28 of the pulse generator serves as a common indifferent electrode. The device can be programmed to operate in the DDD, DVI, VDT/I and VVI mode, but may have numerous resultant modes depending on the programming of the output pulse widths and amplifier sensitivities and on the natural underlying heart rhythm. Such resultant modes can include DAT/I, DVI, DOO, AOO, VOO, VAT, AVI, AAI, ADT/I and OOO.

In the DDD mode, the programmable lower rate establishes the rate at which the pulse generator will pace if no P or R waves are sensed. At this rate the operation is A-V sequential and the interval between atrial and ventricular outputs (the A-V interval) is programmable.

If a P-wave is sensed, it will inhibit an atrial pacing output and trigger the A-V interval circuitry. If an R-wave is sensed prior to the completion or the A-V interval, the ventricular pacing output is inhibited and all timing circuits will be reset. If an R-wave is not sensed prior to the completion of the A-V interval, a ventricular pacing output will occur at the end of the delay.

After an atrial event (sensed P-wave or atrial pacing output) the atrial amplifier is blanked. The ventricular amplifier 12 is also blanked for 15, 6 ms (ventricular blanking) after an atrial output to avoid sensing the voltage induced on the ventricular lead. The atrial amplifier 10 remains off until after the next ventricular event and is turned on only after the ventricular amplifier 12 has been on for 31 ms. This is to help insure that when both amplifiers are being turned back on that possible ectopic events which may occur are sensed first by the ventricular amplifier or are not sensed at all. If both amplifiers are turned on simultaneously, there exists the possibility that a heat depolarization could have just passed by the ventricular electrode and will not be sensed by that amplifier. However, that same event could reach the atrial electrodes later and be regarded as a P-wave starting the A-V interval and causing a ventricular stimulating pulse. Such ectopic events that occur high in the ventricle are likely to be sensed in the atrium. The consequence of the PVC sensed as a P-wave could be to pace on A-V interval later into what may be the repolarization phase of the PVC if the PVC is not sensed by the ventricular sense amplifier. The atrial blanking overlap is described in greater detail in commonly assigned, co-pending U.S. Patent Application Ser. No. 145,052, filed Apr. 30, 1980, by Harold Toby Markowitz.

A P-wave sensed after the atrial amplifier 10 is turned on but before the end of the upper rate period will trigger an A-V interval by the P-R counter 218; however, the pulse generator will wait until the end of the upper rate period before a ventricular output will occur. This implements the upper rate characteristic of the atrial triggering mechanism.

At the time of a ventricular event (sensed R-wave or ventricular pacing output) the ventricular amplifier 12 is turned off or blanked for 125 ms, the upper rate period is started by the upper rate timer/counter 220 (at rates of 100, 125, 150, or 175 bpm) and the 233 ms ventricular refractory is started. During refractory the lower rate timer 216 cannot be reset. The timer 216 will be reset by either a ventricular pacing output or sensed R-wave which occurs outside of the ventricular refractory period. After the ventricular amplifier 12 is turned on and before the end of the 233 ms R-refractory period, a ventricular sense amplifier output will restart the 233 ms refractory period, 125 ms R-blanking, 156 ms atrial blanking and upper rate period.

In the programmed modes DDD or VDT/I, the ventricular amplifier outputs after ventricular blanking and before refractory ends cause another 125 ms ventricular blanking, 156 ms atrial blanking and the ventricular refractory timer to be set to 342 ms (PVC refractory) provided that no preceeding P-wave has been sensed. Thus, there is a window of 342−125=217 ms for a retriggering of refractory. In order for a signal of continuous interference to keep retriggering the ventricular refractory timer (digital reversion) the ventricular amplifier outputs must be no further apart than 342 ms. If the ventricular refractory timer is always retriggered during the 217 ms window then the pacemaker will operate A-V sequential asynchronous (DOO) because the lower rate timer will not be reset from ventricular amplifier outputs. This corresponds to a lowest interference frequency of 2.9 Hz.

However, if the ventricular amplifier output, after ventricular blanking and before refractory end, was preceeded by a sensed P-wave, the R-refractory timer will be set to 233 ms as described hereinbefore.

The pacemaker programmed in the DDD mode will perform in a pseudo-Wenckeback fashion when atrial rates exceed the programmed upper rate. There will be gradual A-V lengthening until an atrial beat does not lead to a ventricular pacing output. The process then repeats. At high upper rates the device will reach 2:1 block dependent upon the programmed A-V interval.

Thus, at a setting of 250 ms A-V interval and 175 bpm upper rate, the device will operate in a 2:1 block at an atrial rate of 148 bpm (ventricular rate=74 bpm) and the upper rate will not be used. If the upper rate were set to 125 bpm the device would exhibit the A-V prolongation/dropped beat characteristic from atrial rates of 125 to 148 bpm. At 148 bpm the ventricular rate would drop to half that of the atrial input. Shorter A-V settings push the 2:1 block point to higher rates. This operation is similar in principle to that shown in commonly assigned U.S. Pat. No. 4,059,116.

This description is presented to describe the best mode in which the following description of the invention may be put into practice.

DESCRIPTION OF THE END-OF-LIFE BEHAVIOR

Figure 3:
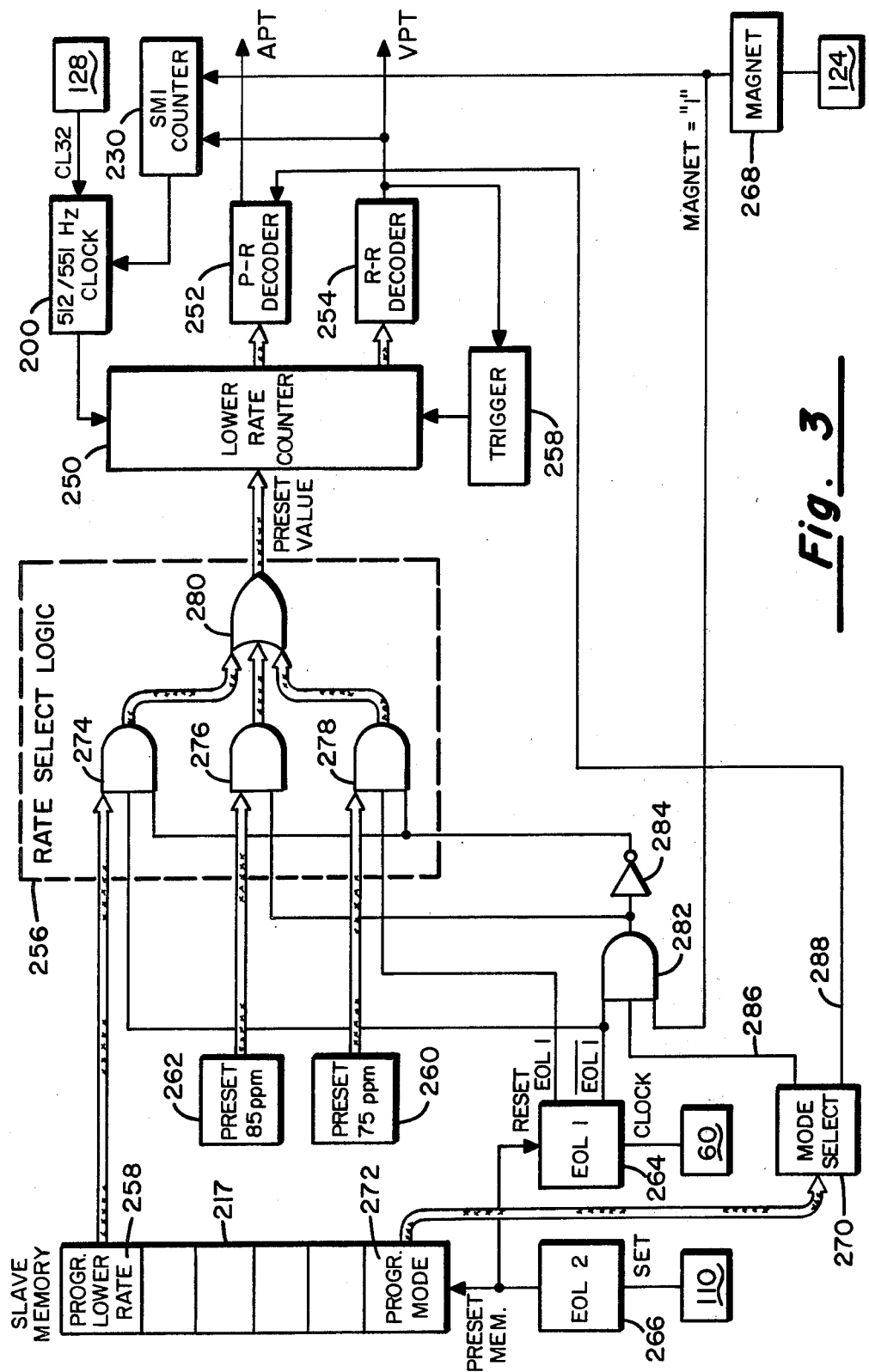
FIG. 3 is a block circuit diagram of the depletion indicating circuit of the pulse generator.

Turning now to the end-of-life operation of the pulse generator of the present invention, TABLE 1 depicts a table of the modes of operation and the rates that the pulse generator exhibits in response to the closure of the reed switch 32 and the presence of none, one or both of the signals EOL1 and EOL2 and FIG. 3 depicts in block diagram form a preferred circuit for achieving the modes and rates of TABLE 1. The battery power source is of the type which decreases in voltage over time, from an initial voltage of 2.8 volts, for example. The battery monitors 56 and 84 are operable to detect the depletions below 2.2 volts and 2.0 volts, respectively for example, to provide the EOL1 and EOL2 signals at terminals 60 and 110. In reference to FIG. 26, the magnet signal at terminal 124 and the EOL1 signal at terminal 60 are coupled to the R-R or lower rate counter 216 and the EOL2 signal at terminal 110 is coupled to the memory 214.

The pacemaker responds to the closure of the reed switch 32 in a manner similar to the response described in the commonly assigned, co-pending U.S. Pat. No. 4,230,120. Briefly, the closure of the reed switch causes the pulse generator to operate in an asynchronous mode wherein the sense amplifier output signals are ignored and at a rate different than the programmed rate. The third synchronous atrial and ventricular output pulses are reduced in width to 75 percent of their programmed (or pulse width stretched) pulse widths. One observing the EKG can thus ascertain that the reed switch is closed so programming or telemetry can commence and the capture or noncapture of the third pulses sequence provides a safety margin indicator (SMI as earlier described).

In the present invention, the resultant modes and rate of pacing (after the third pulse) demonstrate both the programmed mode and the battery depletion level. In reference to TABLE 1, the four normally programmed modes in the leftmost column change on application of the magnet to DOO for the modes DOO, DVI and to VOO for the modes VVI, VDT/I at beginning of life (BOL) and at EOL1. The rates indicate the difference between DDD and DVI and between VVI and VDT/I (AP on the chart indicating "as programmed"). The rates of 85, 75 and 65 are selected since these are rates not contemplated to be programmable rates.

These modes and rates are depicted in the following TABLE 1:

TABLE 1

| Programmed Mode | Magnet Mode | First Three Intervals* | Succeeding Intervals |
|---|---|---|---|
| B.O.L. | | | |
| DDD | DOO | 85 + 10% = 93.5 | 85 |
| DVI | DOO | AP** + 10% | AP** |
| VVI | VOO | AP** + 10% | AP** |
| VDT/I | VOO | 85 + 10% = 93.5 | 85 |
| EOL 1 | | | |
| Imminent Battery Depletion | | | |
| DDD | DOO | 75 + 10% = 82.5 | 75 |
| DVI | DOO | 75 + 10% = 82.5 | 75 |
| VVI | VOO | 75 + 10% = 82.5 | 75 |
| VDT/I | VOO | 75 + 10% = 82.5 | 75 |
| EOL 2 | | | |
| Final Battery Depletion | | | |
| DDD | VOO | 65 + 10% = 71.5 | 65 |
| DVI | VOO | 65 + 10% = 71.5 | 65 |
| VVI | VOO | 65 + 10% = 71.5 | 65 |
| VDT/I | VOO | 65 + 10% = 71.5 | 65 |

*Third ventricular and atrial (DOO mode) stimulus after magnet acceptance will have 75% of actual P.W.
**As programmed.

The magnet mode end safety margin indicating rates of the present invention are plus 10 percent of the rates 85, 75, 65 or AP. Thus, for the first three intervals, the rates are 93.5, 82.5 or 71.5 bpm depending on the EOL condition. Thereafter, the rates are the present test rates of 85, 75 and 65 bpm, respectively. The 10 percent rate change is effected by the SMI counter 230 of FIG. 2a which commences counting output signals VPT of the R-R counter and until three pulses are counted disables a stage in the divider 200 to increase the clock frequency from 512 Hz to 551 Hz. The faster clock frequency when applied to P-R counter 218 and R-R counter 216 causes the 10 percent increase in the respective atrial and ventricular rates.

During sensed B.O.L. conditions (when source voltage exceeds 2.2 volts, for example), the rate of 85 bpm or AP and the asynchronous modes DOO or VOO signify normal conditions and allow the observer to determine the programmed mode. But when source voltage decreases below 2.2 volts, the EOL1 signal coupled to the R-R counter causes the R-R counter to ignore the programmed rate count by presetting the decoding logic between the lower rate data bus and the counter stages and thereby substituting the preset count (corresponding to 75 or 82.5 bpm) for the rate data count in memory 214. Similarly, the P-R counter decoding circuit is loaded with a preset count and one or both (depending on the DOO or VOO mode) counters 216 and 218 are incremented by the slow clock pulses to provide output pulse(s) at the 75 or 82.5 bpm rate.

At EOL1 and magnet application, rate is the same for all programmed modes. Therefore, it is only possible to distinguish the dual and single chamber programmed modes. The EOL1 condition would, in any case, call for closer examination and monitoring of the device because it indicates imminent battery depletion. The observing physician would schedule a procedure to remove and replace the device or prolong its life by changing to a simpler mode, e.g. VVI, or lowering the pacing rate.

When battery voltage decreases below the EOL2 level (e.g. 2.0 volts), the application of the magnet causes the SMI sequence as earlier described and then operates the pulse generator in the VOO Mode regardless of the programmed mode and at a rate of 65 bpm. This indicates to the observing physician that final battery depletion is near and that the unit is to be replaced.

The 65 bpm rate is accomplished at magnet application by operation of logic circuitry within the memory 214 which responds to the EOL2 signal on terminal 110 and advantageously loads in the safety rate of 65 bpm which is hardwired into memory 214. The safety rate thus is directed on L-R data bus line to R-R counter 216 to control the rate in the VOO mode in precedence over the programmed rate. After the removal of the magnet, the pulse generator in this condition does not return to the programmed mode or rate but remains at the 65 bpm rate in the VVI mode to decrease the current demand in the power source. Thus once the EOL2 level is reached and the magnet applied, the safety rate and ode take precedence over the programmed rate and mode. Preferably the pulse generator can no longer be reprogrammed; however, it could be designed to allow the physician to subsequently reprogram the pulse generator. The EOL2 mode and rate indicates to the observing physician that the pulse generator should be replaced as soon as practicable.

Turning now to FIG. 3 there is depicted a block diagram of a circuit for effecting the end-of-life test rates and modes described in reference to TABLE 1 and in the context of FIGS. 1a, 1b and 2a, 2b. The circuit of FIG. 3 responds to the EOL1 signal at terminal 60, the EOL2 signal at terminal 110, the closure of the reed switch at terminal 124, the clock input at terminal 128 and the contents of the mode and rate memory to provide the modes and rates hereinbefore mentioned. The rates are established by the eight stage counter 250 (in the R-R counter 216) which is loaded with selected rate data and downcounted by the 512/551 Hz clock 200 until a first count is obtained which is decoded by the P-R decoder 252 to produce the atrial pace trigger signal APT, and then downcounted to a further predetermined number whereupon the R-R decoder 254 produces the ventricular pace trigger signal VPT. The selected rate count is loaded into the counter 250 by the rate select logic 256 each time the counter 250 is triggered by the trigger logic 258. The selected rate count is one of four possible counts, including the programmed count and the 65 bpm safety rate, both present in the rate memory stages 258, the 75 bpm preset logic circuit 260, and the 85 bpm count of preset logic circuit 262. The selection of the one of the four possible rate counts is controlled by mode select circuit 220 and by the presence or absence of the EOL1 and EOL2 signals which set the respective EOL1 and EOL2 data registers 264 and 266.

The closure of the reed switch 32 (FIG. b) provides a signal at terminal 124 and sets the magnet enable register 268. The setting of the magnet enable register 268 causes the SMI counter 230 to change the clock frequency of clock 200 from 512 Hz to 551 Hz for three R-R cycles of the eight stage counter 250 subsequent to the next following delivery of a ventricular pace trigger VPT. The set state of the magnet enable register 268 is also conveyed to the mode select logic 270 and to the trigger logic 258. The mode select logic 270 receives a further input from the mode memory stages 272 of the memory 214 (FIG. 2a). The mode select logic 270 is triggered by the set state of the magnet enable register 268 to provide an output signal which is applied to the P-R decoder 252 to, in certain instances be described, disable the decoder 252 thus preventing the production of an atrial pace trigger pulse APT. The trigger logic circuit 258 responds to the next occurring VPT signal for providing a trigger signal to the T input of counter 250. The mode data of the mode memory stages 272 is also applied to the P-R decoder 252 to disable the decoder 252 under EOL2 conditions.

At BOL conditions, the registers 264 and 266 are not set. The programmed rate data that is in the rate memory stages 258 is applied to the rate select logic 256 to one input of AND gate 274. In addition, the 85 bpm preset logic 252 provides the 85 bpm preset rate to one input of AND gate 276 in the rate select logic 256. In reference to TABLE 1, if the programmed mode indicated by the mode data from mode memory stages 272 is DVI or VVI, the rate select logic 256 selects the programmed rate and applies it to the counter 250. If the mode data is not DVI nor VVI, the rate select logic 256 is, in response to the trigger signal, preset to 85 bpm by the preset logic 262, and the 85 bpm rate count is loaded into the counter 250. Thus, at BOL the asynchronous pacing rate is either 85 bpm (93.5 bpm for the first three pacing intervals) or the programmed rate, depending on the programmed mode. In either case, the data is loaded into counter 250 through OR gate 280.

The selection of the programmed rate or the 85 bpm rate is accomplished by the mode select 270, the AND gate 282 and the inverter 284. The magnet enable signal and the EOL1 signal are at high logic levels and are applied to inputs of AND gate 282. If the DDD or VDT/I modes are programmed in memory stage 272, then the output on line 286 of mode select 270 is also high and the output of AND gate 282 goes high. The high output is coupled to an input of AND gate 276 and that gate 276 is enabled to pass the 85 bpm count data through OR gate 280 to the counter 250. The other two gates, 274 and 278 are disabled by the low logic level output of inverter 284.

If the programmed modes are DVI or VVI, the output 286 is low, and gate 282 is disabled. Since the EOL1 signal and the output of inverter 284 are high, then the rate count for rate memory stage 258 is transmitted through AND gate 274 and OR gate 280 to load the counter 250.

Ordinarily, in the absence of the magnet enable signal, the EOL1 output of register 264 and the output of inverter 284 are high. The AND gate 274 is therefore enabled, and the gates 276, 278 and 282 are disabled. Thus, the AND gate 274 also, in the ordinary operation of the pulse generator, applies the programmed rate count to the counter 250.

At imminent battery depletion, the EOL1 data register 264 is set causing the EOL1 signal to go high. Thus, the AND gate 278 is enabled and the AND gates 274 and 276 are disabled. When the gate 278 is enabled, the rate select logic 256 supplies the 75 bpm rate count under all programmed conditions to the counter 250.

At final battery depletion the data registers 266 and 264 are set and reset, respectively. Simultaneously, the memory rate count is erased and the hardwired safety rate of 65 bpm is presented to the AND gate 274. In addition, the programmed mode is reset to the VVI mode so that the mode select 270 provides a signal on conductor 288 to disable the P-R decoder. The EOL1 signal is high and the output of AND gate 282 is low, and AND gate 274 is therefore enabled. The rate is therefore set at 65 bpm and the mode is set to the VOO mode at the time that the magnet is applied and to the VVI mode thereafter.

In addition, it is contemplated that the memory may contain hard wired safety or nominal values for other parameters, e.g. the ventricular pulse width (e.g. 0–5 ms), and the ventricular sensitivity (e.g. 2.5 mV). The nominal ventricular pulse width and sensitivity data are substituted for the programmed data and control operation of the pulse generator in the VVI mode at EOL2.

The modes and rates related are arbitrary, but are selected to be distinguishable from normally programmable rates. It is contemplated that different rates could be related to distinguish each mode under each battery depletion condition. It is further contemplated that the end-of-life depletion circuits and modes herein described could as well be applied to pacemakers programmable in only two or more of the modes herein described. The operating modes and parameters of any medical device other than a pacemaker pulse generator may similarly be changed to indicate its power source depletion level. The invention may thus find application in an implantable drug dispenser, nerve or tissue stimulator, blood pump or other medical device dependent on an depletable power source.

The invention may also be implemented in any suitable analog or digital circuitry including software controlled custom or conventional microprocessors. These and other modifications or uses of the invention will be apparent to those skilled in the art.

I claim:

1. A programmable medical device having programmable means responsive to externally applied programming signals for programming the operation of the medical device in one of a plurality of operating modes and operating rates comprising:
   a depletable power source for powering said medical device;
   power source energy detecting means coupled to said power source for providing a first end-of-life signal at a first depletion level and a second end-of-life signal at a second depletion level lower than said first depletion level;
   first rate and mode switching means coupled to said programmable means and said detecting means and responsive to an externally applied testing signal for operating said medical device in a first predetermined mode and at the programmed rate when neither a first nor a second end-of-life signal is present;
   second rate and mode switching means coupled to said programmable means and said detecting means and responsive to said testing signal for operating said medical device in the first predetermined mode and at a first predetermined rate when said first end-of-life signal is present; and
   third rate and mode switching means coupled to said programmable means and said detecting means and responsive to said testing signal for operating said medical device in a second predetermined mode and rate when said second end-of-life signal is present.

2. The programmable medical device of claim 1 wherein said first rate and mode switching means further comprises selecting means responsive to the programmed mode for operating said medical device at a third predetermined rate when said programmable means is programmed to a certain operating mode and at said programmed rate when said programmable means is programmed to a further operating mode.

3. The programmable medical device of claim 2 wherein said third rate and mode switching means further comprises means for changing the programmed rate in said programmable means to said second predetermined rate.

4. The programmable medical device of claim 2 wherein said third rate and mode switching means further comprises means for changing the programmed mode in said programmable means to said second predetermined mode.

5. The programmable medical device of claim 1 wherein said third rate and mode switching means further comprises means for changing the programmed rate in said programmable means to said second predetermined rate.

6. The programmable medical device of claim 5 wherein said third rate and mode switching means further comprises means for changing the programmed mode in said programmable means to said second predetermined mode.

7. The programmable medical device of claim 1 wherein said third rate and mode switching means further comprises means for changing the programmed mode in said programmable means to said second predetermined mode.

8. The programmable medical device of claim 1 further comprising pulse generating means for providing tissue stimulating pulses at said operating rates.

9. A programmable atrial and ventricular pulse generator comprising:
   a depletable power source for powering said pulse generator;
   power source energy detecting means coupled to said power source for providing a first end-of-life signal at a first depletion level and a second end-of-life signal at a second depletion level lower than said first depletion level;
   atrial sensing means for sensing atrial contractions of the heart and providing an atrial sense signal;
   ventricular sensing means for sensing ventricular contractions of the heart and providing a ventricular sense signal;
   atrial pulse providing means for providing atrial stimulating pulses;
   ventricular pulse providing means for providing ventricular stimulating pulses; and
   digital control and memory means responding to atrial and ventricular sense signals, and selectively triggering said atrial and ventricular pulse providing means under the control of operating mode and rate control signals, further comprising:
   programmable memory means for storing operating mode and rate control signals;
   first rate and mode switching means coupled to said programmable means and said detecting means and responsive to an externally applied testing signal for triggering said atrial and ventricular pulse providing means in a first predetermined, non-programmed mode and at the programmed rate when neither a first nor a second end-of-life signal is present;
   second rate and mode switching means coupled to said programmable means and said detecting means and responsive to said testing signal for triggering said atrial and ventricular pulse providing means in the first predetermined, non-programmed mode and at a first predetermined rate when said first end-of-life signal is present; and third rate and mode switching means coupled to said programmable means and said detecting means and responsive to said testing signal for triggering said ventricular pulse providing means in a second predetermined non-programmed mode and at a second predetermined rate when said second end-of-life signal is present.

10. The programmable medical device of claim 9 wherein said first rate and mode switching means further comprises selecting means responsive to the programmed mode for operating said pulse generator at a third predetermined rate when said programmable means is programmed to a certain operating mode and at said programmed rate when said programmable means is programmed to a further operating mode.

11. The programmable medical device of claim 10 wherein said third rate and mode switching means further comprises means for changing the programmed rate in said programmable memory means to said second predetermined rate.

12. The programmable medical device of claim 10 wherein said third rate and mode switching means further comprises means for changing the programmed mode in said programmable means to said second predetermined, non-programmed mode.

13. The programmable medical device of claim 9 wherein said third rate and mode switching means further comprises means for changing the programmed rate in said programmable memory means to said second predetermined rate.

14. The programmable medical device of claim 13 wherein said third rate and mode switching means further comprises means for changing the programmed mode in said programmable means to said second predetermined, non-programmed mode.

15. The programmable medical device of claim 9 wherein said third rate and mode switching means further comprises means for changing the programmed mode in said programmable memory means to said second predetermined, non-programmed mode.

16. A programmable atrial and ventricular pulse generator comprising:
a depletable power source for powering said pulse generator;
atrial pulse providing means for providing atrial stimulating pulses;
ventricular pulse providing means for providing ventricular stimulating pulses; and
power source energy detecting means coupled to said power source for providing a first end-of-life signal at a first depletion level and second end-of-life signal at a second depletion level lower than said first depletion level;
digital control and memory means responding to atrial and ventricular sense signals, and selectively triggering said atrial and ventricular pulse providing means under the control of operating mode and rate control signals, further comprising:
programmable memory means for selectively storing operating mode and rate control signals, a first of said selectively stored operating mode signals providing for the operation of said pulse generator in an atrial and ventricular pacing mode and a second of said selectively stored operating mode signal providing for the operation of said pulse generator in a ventricular pacing mode;
first rate and mode switching means coupled to said programmable memory means and said detecting means and responsive to an externally applied testing signal for triggering said atrial and ventricular pulse providing means in said atrial and ventricular pacing mode and at a first fixed rate when said programmable memory means stores said first selectively stored operating mode signal and in said ventricular pacing mode and at said first fixed rate when said programmable memory means stores said second selectively stored operating mode signals when neither a first nor a second end-of-life signal is present.

17. The pulse generator of claim 16 wherein said digital control and memory means further comprises:
second rate and mode switching means coupled to said programmable means and said detecting means and responsive to said testing signal for triggering said atrial and ventricular pulse providing means at a second fixed rate when said first end-of-life signal is present and in said atrial and ventricular pacing mode when said programmable memory means stores said first selectively stored operating mode signal and in said ventricular pacing mode when said programmable memory means stores said second selectively stored operating mode signal.

18. The pulse generator of claim 17 wherein said digital control and memory means further comprises:
third rate and mode switching means coupled to said programmable means and said detecting means and responsive to said testing signal for triggering said ventricular pulse providing means at a third fixed rate when said second end-of-life signal is present and in said ventricular pacing mode regardless of the stored operating mode signal.

19. The pulse generator of claim 18 wherein:
said memory means further comprises means for operating said pulse generator at a non-programmable fixed safety rate and in the ventricular pacing mode in the absence of any stored operating mode and rate control signal; and
said third rate and mode switching means is operative to erase the stored operating mode and rate control signal of said memory means.

20. The pulse generator of claim 16 wherein said digital control and memory means further comprises:
third rate and mode switching means coupled to said programmable means and said detecting means and responsive to said testing signal for triggering said ventricular pulse providing means at a third fixed rate when said second end-of-life signal is present and in said ventricular pacing mode regardless of the stored operating mode signal.

21. The pulse generator of claim 20 wherein:
said memory means further comprises means for operating said pulse generator at a non-programmable fixed safety rate and in the ventricular pacing mode in the absence of any stored operating mode and rate control signal; and
said third rate and mode switching means is operative to erase the stored operating mode and rate control signal of said memory means.

22. A programmable atrial and ventricular pulse generator comprising:
a depletable power source for powering said pulse generator;
power source energy detecting means coupled to said power source for providing an end-of-life signal when said power source energy depletes to a certain depletion level; and atrial sensing means for sensing atrial contractions of the heart and providing an atrial sense signal;

ventricular sensing means for sensing ventricular contractions of the heart and providing a ventricular sense signal;

atrial pulse providing means for providing atrial stimulating pulses;

ventricular pulse providing means for providing ventricular stimulating pulses; and digital control and memory means responsive to atrial and ventricular sense signals, and selectively triggering said atrial and ventricular pulse providing means under the control of stored operating mode and rate control memory data further comprising:

means for operating said pulse generator at a non-programmable safety rate and in low energy consuming mode in the absence of any stored operating mode and rate control signal; and mode and rate switching means responsive to said end-of-life signal for disregarding any stored operating mode and rate control date in said memory means and for operating said pulse generator at said safety rate and in said low energy consuming mode.

23. The pulse generator of claim 22 wherein said pulse generator comprises means responsive to the operation of said memory means in said low energy consuming mode for operating said pulse generator in the fixed rate ventricular pacing mode.

24. The pulse generator of claim 22 wherein said mode and rate switching means is responsive to an externally applied testing signal for erasing any stored operating mode and rate control signal from said memory means when said end-of-life signal is present.

25. A programmable atrial and ventricular pulse generator comprising:

atrial sensing means for sensing atrial contractions of the heart and providing an atrial sense signal;

ventricular sensing means for sensing ventricular contractions of the heart and providing a ventricular sense signal;

atrial pulse providing means for providing atrial stimulating pulses;

ventricular pulse providing means for providing ventricular stimulating pulses; and digital control and memory means responding to atrial and ventricular sense signals, and selectively triggering said atrial and ventricular pulse providing means under the control of operating mode and rate control signals, further comprising:

programmable memory means having memory stages for storing operating mode and rate control data for the selection of the lower pacing rate and the operation of the pulse generator in (1) a DDD mode wherein atrial and ventricular sense signals control the operation of said atrial and ventricular pulse providing means; (2) a DVI mode wherein ventricular sense signals control the operation of said atrial and ventricular pulse providing means; (3) a VVI mode wherein ventricular sense signals control the operation of said ventricular pulse providing means; and (4) a VDT/I mode wherein atrial and ventricular sense signals control the operation of said ventricular pulse providing means;

means for providing a test pacing rate; and rate and mode switching means responsive to an externally applied testing signal for operating said pulse generator at said test pacing rate and (1) in the DOO mode, wherein atrial and ventricular stimulating pulses are provided at said test pacing rate, when said memory stages store the DDD operating data and (2) in the VOO mode, wherein ventricular pulses are provided at said fixed rate when said memory stages store the VDT/I operating mode data and at the rate provided by the rate control data and (1) in the DOO mode when said memory stages store the DVI operating data and (2) in the VOO mode when said memory stages stored the VVI operating data.

26. The pulse generator of claim 25 further comprising:

a depletable power source for powering said pulse generator;

power source energy detecting means coupled to said power source for providing a first end-of-life signal at a first depletion level and a second end-of-life signal at a second depletion level lower than said first depletion level.

27. The pulse generator of claim 26 wherein said digital control and memory means further comprises:

second rate and mode switching means coupled to said programmable means and said detecting means and responsive to said testing signal for triggering said atrial and ventricular pulse providing means at a second fixed rate when said first end-of-life signal is present and in said atrial and ventricular pacing mode when said programmable memory means stores said first selectively stored operating mode signal and in said ventricular pacing mode when said programmable memory means stores said second selectively stored operating mode signal.

28. The pulse generator of claim 27 wherein said digital control and memory means further comprises:

third rate and mode switching means coupled to said programmable means and said detecting means and responsive to said testing signal for triggering said ventricular pulse providing means at a third fixed rate when said second end-of-life signal is present and in said ventricular pacing mode regardless of the stored operating mode signal.

29. The pulse generator of claim 28 wherein:

said memory means further comprises means for operating said pulse generator at a non-programmable fixed safety rate and in the ventricular pacing mode in the absence of any stored operating mode and rate control signal; and said third rate and mode switching means is operative to erase the stored operating mode and rate control signal of said memory means.

30. A programmable medical device having programmable means responsive to externally applied programming signals for programming the operation of the medical device in one of a plurality of operating modes and operating rates comprising:

a depletable power source for powering said medical device;

power source energy detecting means coupled to said power source for providing an end-of-life signal at an energy depletion level; and digital control and memory means responsive to stored operating mode and rate control data for selectively operating said medical device further comprising:

means for operating said pulse generator at a non-programmable safety rate and in low energy consuming mode in the absence of any stored operating mode and rate control data; and mode and rate switching means responsive to said end-of-life signal for disregarding any stored operating mode and rate control data in said memory means and for operating said medical device at said safety rate and in said low energy consuming mode.

* * * * *

UNITED STATES PATENT AND TRADEMARK OFFICE
CERTIFICATE OF CORRECTION

PATENT NO. : 4,390,020

DATED : June 28, 1983

INVENTOR(S) : Lodewijk-Jozef Herpers

Page 1 of 3

It is certified that error appears in the above-identified patent and that said Letters Patent are hereby corrected as shown below: On the title page

[22] Filed: "Feb. 17, 1983" should be --Feb. 17, 1981--;

Column 6,
    Line 17, remove "and";

Column 9,
    Line 52, "FIG. 2" should be --FIGS. 2a and 2b--;

Line 52, "FIG. 2" should be --FIGS. 2a and 2b--;

Column 10,
    Line 33, "the" should be --that--;

Column 15,
    Line 37, "FIG. 26" should be -- FIG. 2b--;

Column 16,
    Line 30, "present" should be --preset--;

Column 17,
    Line 17, "ode" should be --mode--;

Column 17,
    Line 54, "(FIG. b)" should be --(FIB. 1b)--;

Column 18,
    Line 29, "EOL1" should be --$\overline{\text{EOL1}}$--;

Line 40, "EOL1" should be --$\overline{\text{EOL1}}$--;

Line 46, "EOL1" should be --$\overline{\text{EOL1}}$--;

Line 65, "EOL1" should be --$\overline{\text{EOL1}}$--;

UNITED STATES PATENT AND TRADEMARK OFFICE
CERTIFICATE OF CORRECTION

PATENT NO. : 4,390,020
DATED : June 28, 1983
INVENTOR(S) : Lodewijk-Jozef Herpers Page 2 of 3

It is certified that error appears in the above-identified patent and that said Letters Patent are hereby corrected as shown below:

Column 20,

Line 18, "claim 5" should be --claim 2--;

Line 23, "claim 1" should be --claim 3--;

Column 21,

Line 18, "claim 10" should be --claim 9--;

Line 26, "mode" should be --rate--;

Line 26, after "programmable" insert --memory--;

Line 27, remove ", non-programmed mode" and insert --rate--:

Line 31, "rate" should be -- mode --;

Line 32, remove "rate" and insert --non-programmed mode--;

UNITED STATES PATENT AND TRADEMARK OFFICE
CERTIFICATE OF CORRECTION

PATENT NO. : 4,390,020
DATED : June 28, 1983
INVENTOR(S) : Lodewijk-Jozef Herpers It is certified that error appears in the above-identified patent and that said Letters Patent are hereby corrected as shown below:

Column 21,
    Line 33, "claim 13" should be --claim 10--;

Line 38, "claim 9" should be --claim 11--;

Line 41, remove "memory".

*Signed and Sealed this*

*Twenty-seventh* Day of *March 1984*

[SEAL]

*Attest:*

GERALD J. MOSSINGHOFF

*Attesting Officer*     *Commissioner of Patents and Trademarks*